United States Patent
Bari et al.

(10) Patent No.: US 11,390,658 B2
(45) Date of Patent: Jul. 19, 2022

(54) ANTI-CD7 CHIMERIC ANTIGEN RECEPTOR AND METHOD OF USE THEREOF

(71) Applicant: ST. JUDE CHILDREN'S RESEARCH HOSPITAL, Memphis, TN (US)

(72) Inventors: Rafijul Bari, Gaithersburg, MD (US); Wing Leung, Memphis, TN (US)

(73) Assignee: ST. JUDE CHILDREN'S RESEARCH HOSPITAL, Memphis, TN (US)

( * ) Notice: Subject to any disclaimer, the term of this patent is extended or adjusted under 35 U.S.C. 154(b) by 749 days.

(21) Appl. No.: 16/307,201

(22) PCT Filed: Jun. 2, 2017

(86) PCT No.: PCT/US2017/035624
§ 371 (c)(1),
(2) Date: Dec. 5, 2018

(87) PCT Pub. No.: WO2017/213979
PCT Pub. Date: Dec. 14, 2017

(65) Prior Publication Data
US 2019/0144522 A1    May 16, 2019

Related U.S. Application Data

(60) Provisional application No. 62/346,092, filed on Jun. 6, 2016.

(51) Int. Cl.
| | |
|---|---|
| *C07K 16/28* | (2006.01) |
| *C07K 14/725* | (2006.01) |
| *A61P 35/00* | (2006.01) |
| *A61K 35/17* | (2015.01) |
| *C07K 14/705* | (2006.01) |
| *A61K 35/15* | (2015.01) |
| *A61K 48/00* | (2006.01) |
| *C07K 14/73* | (2006.01) |
| *A61K 38/00* | (2006.01) |

(52) U.S. Cl.
CPC .......... *C07K 14/7051* (2013.01); *A61K 35/15* (2013.01); *A61K 35/17* (2013.01); *A61K 48/00* (2013.01); *A61P 35/00* (2018.01); *C07K 14/705* (2013.01); *C07K 14/70507* (2013.01); *C07K 14/70514* (2013.01); *C07K 14/70517* (2013.01); *C07K 14/70521* (2013.01); *C07K 14/70578* (2013.01); *C07K 14/70596* (2013.01); *C07K 16/2803* (2013.01); *A61K 38/00* (2013.01); *C07K 2317/55* (2013.01); *C07K 2317/622* (2013.01); *C07K 2319/02* (2013.01); *C07K 2319/03* (2013.01); *C07K 2319/033* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 2015/0118202 A1 | 4/2015 | June | |
| 2016/0045551 A1 | 2/2016 | Brentjens | |
| 2019/0345217 A1* | 11/2019 | Ma | A61K 48/00 |

FOREIGN PATENT DOCUMENTS

| | | |
|---|---|---|
| WO | 2003051926 A2 | 6/2003 |
| WO | 2016138491 A1 | 1/2016 |

OTHER PUBLICATIONS

Brentjens, R, R. Yeh, Y. Bemal, I. Riviere and M. Sadelain (2010) "Treatment of Chronic Lymphocytic Leukemia With Genetically Targeted Autologous T Cells: Case Report of an Unforeseen Adverse Event in a Phase I Clinical Trial." Mol. Ther. 18(4):666-668.

Cruse, J.M., R.E. Lewis, S. Pierce, J. Lam, Y. Tadros (2005) "Aberrant expression of CD7, CD56, and CD79a antigens in acute myeloid leukemias." Exp. Mol. Pathol. 79(1):39-41.

Morgan, R.A., J.C. Yang, M. Kitano, M.E. Dudley, C.M. Laurencot and S.A. Rosenberg (2010) "Case report of a serious adverse event following the administration of T cells transduced with a chimeric antigen receptor recognizing ERBB2." Mol. Ther. 18(4):843-851.

Rogers, S.L., Y. Zhao, X. Jiang, C.J. Eaves, D.L. Mager and A. Rouhi (2010) "Expression of the leukemic prognostic marker CD7 is linked to epigenetic modifications in chronic myeloid leukemia." Mol. Cancer 9:41.

Satoh, C., H. Tamura, T. Yamashita, T. Tsuji, K. Dan and K. Ogata (2009) "Aggressive characteristics of myeloblasts expressing CD7 in myelodysplastic syndromes." Leuk. Res. 33(2):326-31.

Seegmiller, A.C., N.J. Karandikar, S.H. Kroft, R.W. McKenna and Y. Xu (2009) "Overexpression of CD7 in classical Hodgkin lymphoma-infiltrating T lymphocytes." Cytometry B (Clin. Cytom.) 76B:169-74.

(Continued)

*Primary Examiner* — Zachary S Skelding
(74) *Attorney, Agent, or Firm* — Licata & Tyrrell P.C.

(57) ABSTRACT

A nucleic acid construct and mammalian cell harboring nucleic acids encoding an anti-CD7 chimeric antigen receptor are provided. Methods for treating cancer, in particular a hematologic cancer, using the nucleic acid construct or mammalian cell are also described.

6 Claims, 3 Drawing Sheets
Specification includes a Sequence Listing.

(56) References Cited

OTHER PUBLICATIONS

Till, B.G., M.C. Jensen, J. Wang, E.Y. Chen, B.L. Wood, H.A. Greisman, X. Qian, S.E. James, A. Raubitschek, S.J. Forman, A.K. Gopal, J.M. Pagel, C.G. Lingren, P.D. Greenberg, S.R. Riddell and O.W. Press (2008) "Adoptive immunotherapy for indolent non-Hodgkin lymphoma and mantle cell lymphoma using genetically modified autologous CD20-specific T cells." Blood 112(6):2261-2271.
International Search Report and Written Opinion in PCT/US17/35624 dated Aug. 25, 2017.
International Preliminary Report on Patentability in PCT/US17/35624 dated Dec. 11, 2018.

* cited by examiner

SEQUENCE LISTING

<160> NUMBER OF SEQ ID NOS: 13

<210> SEQ ID NO 1
<211> LENGTH: 1545
<212> TYPE: DNA
<213> ORGANISM: Artificial Sequence
<220> FEATURE:
<223> OTHER INFORMATION: Synthetic nucleotide sequence molecule.

<400> SEQUENCE: 1

```
cgaattcgcc gccaccatgg ccttaccagt gaccgccttg ctcctgccgc tggccttgct      60
gctccacgcc gccaggccgg cggccgcgac gtcgggcccc agtcaggacc tggtctggtg     120
aaaccttctc agacagtgtc cctcacctgc actgtcactg gcatctccat caccactgga     180
aattacagat ggagctggat ccggcagttt ccaggaaaca aactggagtg gatagggtac     240
atatactaca gtggaatcat tacctataat ccatctcgca caagtcgaac caccatcact     300
agagacattt ccaagaacca attcttcctg gaaatgaact ctttgactgc tgaagacaca     360
gccacatact actgtgcacg agagagaggg atctactatg attccctatg gtacttcgat     420
```

```
gtctggggcg cagggaccac ggtcaccgtc tcctcagcca aaacgacacc cgggagtgca    480
tccgccccaa agcttgaaga aggtgaattt tcagaagcac gcgtagatat cgtgctcacc    540
caatctccag caatcatgtc tgcatctcca ggggagaagg tcaccataac ctgcagtgcc    600
agctcaagtg taagttccag ttacttgcac tggtaccagc agaagtcagg tgcctccccc    660
aaactctgca tttatagcac atccaacttg gcttctggag tccctgctcg cttcagtggc    720
agtgggtctg ggacctctta ctctctcaca atcagccgaa tggggggctga agatgctgcc    780 acttattact gccaacaaag gagtggttac ccattcacgt tcggctcggg gacaaagttg    840
gaaataaaac gggctgatgc tccgcgggtc gacaccacga cgccagcgcc gcgaccacca    900
acaccggcgc ccaccatcgc gtcgcagccc ctgtccctgc cccagaggc gtgccggcca    960 gcggcggggg gcgcagtgca cacgaggggg ctggacttcg cctgtgatat ctacatctgg   1020
gcgcccttgg ccgggacttg tgggtccttc tcctgtcac tggttatcac cctttactgc    1080
aaacggggca gaaagaaact cctgtatata ttcaaacaac catttatgag accagtacaa    1140
actactcaag aggaagatgg ctgtagctgc cgatttccag aagaagaaga aggaggatgt    1200
gaactgagag tgaagttcag caggagcgca gacgccccccg cgtaccagca gggccagaac    1260
cagctctata cgagctcaa tctaggacga agagaggagt acgatgtttt ggacaagaga    1320
cgtggccggg accctgagat ggggggaaag ccgagaagga agaaccctca ggaaggcctg    1380
tacaatgaac tgcagaaaga taagatggcg gaggcctaca gtgagattgg gatgaaaggc    1440
gagcgccgga ggggcaaggg gcacgatggc ctttaccagg gtctcagtac agccaccaag    1500
gacacctacg acgcccttca catgcaggcc ctgccccctc gctaa                   1545

<210> SEQ ID NO 2
<211> LENGTH: 514
<212> TYPE: PRT
<213> ORGANISM: Artificial Sequence
<220> FEATURE:
<223> OTHER INFORMATION: Synthetic polypeptide.

<400> SEQUENCE: 2

Arg Ile Arg Arg His His Gly Leu Thr Ser Asp Arg Leu Ala Pro Ala
1               5                   10                  15

Ala Gly Leu Ala Ala Pro Arg Arg Gln Ala Gly Gly Arg Asp Val Gly
            20                  25                  30

Pro Gln Ser Gly Pro Gly Leu Val Lys Pro Ser Gln Thr Val Ser Leu
        35                  40                  45

Thr Cys Thr Val Thr Gly Ile Ser Ile Thr Thr Gly Asn Tyr Arg Trp
    50                  55                  60

Ser Trp Ile Arg Gln Phe Pro Gly Asn Lys Leu Glu Trp Ile Gly Tyr
65                  70                  75                  80

Ile Tyr Tyr Ser Gly Ile Ile Thr Tyr Asn Pro Ser Arg Thr Ser Arg
                85                  90                  95

Thr Thr Ile Thr Arg Asp Ile Ser Lys Asn Gln Phe Phe Leu Glu Met
            100                 105                 110

Asn Ser Leu Thr Ala Glu Asp Thr Ala Thr Tyr Tyr Cys Ala Arg Glu
        115                 120                 125

Arg Gly Ile Tyr Tyr Asp Ser Leu Trp Tyr Phe Asp Val Trp Gly Ala
    130                 135                 140

Gly Thr Thr Val Thr Val Ser Ser Ala Lys Thr Thr Pro Gly Ser Ala
145                 150                 155                 160

Ser Ala Pro Lys Leu Glu Glu Gly Glu Phe Ser Glu Ala Arg Val Asp
```

```
                165                 170                 175
Ile Val Leu Thr Gln Ser Pro Ala Ile Met Ser Ala Ser Pro Gly Glu
            180                 185                 190

Lys Val Thr Ile Thr Cys Ser Ala Ser Ser Val Ser Ser Ser Tyr
            195                 200                 205

Leu His Trp Tyr Gln Gln Lys Ser Gly Ala Ser Pro Lys Leu Cys Ile
    210                 215                 220

Tyr Ser Thr Ser Asn Leu Ala Ser Gly Val Pro Ala Arg Phe Ser Gly
225                 230                 235                 240

Ser Gly Ser Gly Thr Ser Tyr Ser Leu Thr Ile Ser Arg Met Gly Ala
            245                 250                 255

Glu Asp Ala Ala Thr Tyr Tyr Cys Gln Gln Arg Ser Gly Tyr Pro Phe
            260                 265                 270

Thr Phe Gly Ser Gly Thr Lys Leu Glu Ile Lys Arg Ala Asp Ala Pro
            275                 280                 285

Arg Val Asp Thr Thr Thr Pro Ala Pro Arg Pro Pro Thr Pro Ala Pro
            290                 295                 300

Thr Ile Ala Ser Gln Pro Leu Ser Leu Arg Pro Glu Ala Cys Arg Pro
305                 310                 315                 320

Ala Ala Gly Gly Ala Val His Thr Arg Gly Leu Asp Phe Ala Cys Asp
            325                 330                 335

Ile Tyr Ile Trp Ala Pro Leu Ala Gly Thr Cys Gly Val Leu Leu Leu
            340                 345                 350

Ser Leu Val Ile Thr Leu Tyr Cys Lys Arg Gly Arg Lys Lys Leu Leu
            355                 360                 365

Tyr Ile Phe Lys Gln Pro Phe Met Arg Pro Val Gln Thr Thr Gln Glu
    370                 375                 380

Glu Asp Gly Cys Ser Cys Arg Phe Pro Glu Glu Glu Gly Gly Cys
385                 390                 395                 400

Glu Leu Arg Val Lys Phe Ser Arg Ser Ala Asp Ala Pro Ala Tyr Gln
            405                 410                 415

Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
            435                 440                 445

Gly Lys Pro Arg Arg Lys Asn Pro Gln Glu Gly Leu Tyr Asn Glu Leu
            450                 455                 460

Gln Lys Asp Lys Met Ala Glu Ala Tyr Ser Glu Ile Gly Met Lys Gly
465                 470                 475                 480

Glu Arg Arg Arg Gly Lys Gly His Asp Gly Leu Tyr Gln Gly Leu Ser
            485                 490                 495

Thr Ala Thr Lys Asp Thr Tyr Asp Ala Leu His Met Gln Ala Leu Pro
            500                 505                 510

Pro Arg

<210> SEQ ID NO 3
<211> LENGTH: 19
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (1)..(1)
<223> OTHER INFORMATION: Xaa denotes Asp or Glu.
<220> FEATURE:
```

```
<221> NAME/KEY: MISC_FEATURE
<222> LOCATION: (2)..(3)
<223> OTHER INFORMATION: Xaa denotes any amino acid residue.
<220> FEATURE:
<221> NAME/KEY: MISC_FEATURE
<222> LOCATION: (5)..(6)
<223> OTHER INFORMATION: Xaa denotes any amino acid residue.
<220> FEATURE:
<221> NAME/KEY: MISC_FEATURE
<222> LOCATION: (7)..(7)
<223> OTHER INFORMATION: Xaa denotes Ile or Leu.
<220> FEATURE:
<221> NAME/KEY: MISC_FEATURE
<222> LOCATION: (8)..(13)
<223> OTHER INFORMATION: Xaa denotes any amino acid residue.
<220> FEATURE:
<221> NAME/KEY: MISC_FEATURE
<222> LOCATION: (14)..(15)
<223> OTHER INFORMATION: Xaa is present or absent and when present
     denotes any amino acid residue.
<220> FEATURE:
<221> NAME/KEY: MISC_FEATURE
<222> LOCATION: (17)..(18)
<223> OTHER INFORMATION: Xaa denotes any amino acid residue.
<220> FEATURE:
<221> NAME/KEY: MISC_FEATURE
<222> LOCATION: (19)..(19)
<223> OTHER INFORMATION: Xaa denotes Ile or Leu.

<400> SEQUENCE: 3

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 4
<211> LENGTH: 63
<212> TYPE: PRT
<213> ORGANISM: Artificial Sequence
<220> FEATURE:
<223> OTHER INFORMATION: Synthetic polypeptide.

<400> SEQUENCE: 4

Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60

<210> SEQ ID NO 5
<211> LENGTH: 20
<212> TYPE: PRT
<213> ORGANISM: Artificial Sequence
<220> FEATURE:
<223> OTHER INFORMATION: Synthetic polypeptide.

<400> SEQUENCE: 5

Leu Leu Cys Phe Met Leu Leu Leu Leu Ser Gly Asp Val Glu Leu
1               5                   10                  15

Asn Pro Gly Pro
            20

<210> SEQ ID NO 6
<211> LENGTH: 20
<212> TYPE: PRT
<213> ORGANISM: Artificial Sequence
```

```
<220> FEATURE:
<223> OTHER INFORMATION: Synthetic polypeptide.

<400> SEQUENCE: 6

His His Phe Met Phe Leu Leu Leu Leu Ala Gly Asp Ile Glu Leu
1               5                   10                  15

Asn Pro Gly Pro
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic polypeptide.

<400> SEQUENCE: 7

Trp Phe Leu Val Leu Leu Ser Phe Ile Leu Ser Gly Asp Ile Glu Val
1               5                   10                  15

Asn Pro Gly Pro
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic polypeptide.

<400> SEQUENCE: 8

Lys Asn Cys Ala Met Tyr Met Leu Leu Leu Ser Gly Asp Val Glu Thr
1               5                   10                  15

Asn Pro Gly Pro
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic polypeptide.

<400> SEQUENCE: 9

Met Val Ile Ser Gln Leu Met Leu Lys Leu Ala Gly Asp Val Glu Glu
1               5                   10                  15

Asn Pro Gly Pro
            20

<210> SEQ ID NO 10
<211> LENGTH: 22
<212> TYPE: PRT
<213> ORGANISM: Artificial Sequence
<220> FEATURE:
<223> OTHER INFORMATION: Synthetic polypeptide.

<400> SEQUENCE: 10

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 11
<211> LENGTH: 21
<212> TYPE: PRT
```

```
<213> ORGANISM: Artificial Sequence
<220> FEATURE:
<223> OTHER INFORMATION: Synthetic polypeptide.

<400> SEQUENCE: 11

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 12
<211> LENGTH: 23
<212> TYPE: PRT
<213> ORGANISM: Artificial Sequence
<220> FEATURE:
<223> OTHER INFORMATION: Synthetic polypeptide.

<400> SEQUENCE: 12

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 13
<211> LENGTH: 8
<212> TYPE: PRT
<213> ORGANISM: Artificial Sequence
<220> FEATURE:
<223> OTHER INFORMATION: Synthetic polypeptide.
<220> FEATURE:
<221> NAME/KEY: MISC_FEATURE
<222> LOCATION: (2)..(2)
<223> OTHER INFORMATION: Xaa denotes any amino acid residue.
<220> FEATURE:
<221> NAME/KEY: MISC_FEATURE
<222> LOCATION: (4)..(4)
<223> OTHER INFORMATION: Xaa denotes any amino acid residue.

<400> SEQUENCE: 13

Asp Xaa Glu Xaa Asn Pro Gly Pro
1               5
```

ANTI-CD7 CHIMERIC ANTIGEN RECEPTOR AND METHOD OF USE THEREOF

INTRODUCTION

This application is a U.S. National Stage Application of PCT/US2017/035624 filed Jun. 2, 2017 and claims benefit of priority to U.S. Provisional Application Ser. No. 62/346,092, filed Jun. 6, 2016, the contents of each of which is are incorporated herein by reference in their entirety.

BACKGROUND

Patients having B-cell malignancies, including chronic lymphocytic leukemia (CLL), have few treatment options. One approach to treating these patients is to genetically modify T cells to target antigens expressed on tumor cells through the expression of chimeric antigen receptors (CARs). CARs are antigen receptors that are designed to recognize cell surface antigens in a human leukocyte antigen-independent manner. Attempts in using genetically modified cells expressing CARs to treat these types of patients have met with very limited success. See for example, Brentjens, et al. (2010) Mol. Ther. 18:4, 666-668; Morgan, et al. (2010) Mol. Ther. 18:843-851; and Till, et al. (2008) Blood 112:2261-2271.

In most cancers, tumor-specific antigens are not yet well-defined. However, expression of CD7 has been linked to epigenetic modifications in chronic myeloid leukemia (Rogers, et al. (2010) Mol. Cancer 9:41) and has been shown to be overexpressed in classical Hodgkin lymphoma-infiltrating T lymphocytes (Seegmiller, et al. (2009) Cytometry B Clin. Cytom. 76(3):169-74). In addition, CD7 expression has been associated with low remission rates and biological aggressiveness in a significant proportion of acute leukemias (Cruse, et al. (2005) Exp. Mol. Pathol. 79:39-41). Moreover, CD7 positivity in myelodysplastic syndromes has been associated with aggressive characteristics and poor prognosis (Satoh, et al. (2009) Leuk. Res. 33(2):326-31).

SUMMARY OF THE INVENTION

This invention provides an isolated nucleic acid construct encoding a chimeric antigen receptor (CAR) composed of an anti-CD7 binding domain, a transmembrane domain, and a cytoplasmic domain, wherein in certain embodiments, the cytoplasmic domain includes a costimulatory signaling domain and a CD3 signaling domain. In other embodiments, the anti-CD7 binding domain is an antibody or an antigen-binding fragment thereof, e.g., a Fab or a scFv. In further embodiments, the costimulatory signaling domain is the intracellular domain of a costimulatory molecule selected from the group consisting of CD2, CD4, CD5, CD8α, CD8β, CD27, CD28, 4-1BB (CD137), OX40, CD30, CD40, PD-1, ICOS, lymphocyte function-associated antigen-1 (LFA-1), LIGHT, NKG2C, B7-H3, and a ligand that specifically binds with CD83 and any combination thereof. A vector, mammalian cell (e.g., a T cell, a Natural Killer (NK) cell, a cytotoxic T lymphocyte (CTL), or a regulatory T cell) and methods for producing an anti-CD7 CAR T cell and treating cancer, e.g., a hematologic cancer, using the nucleic acid construct or mammalian cell harboring the same are also provided.

DETAILED DESCRIPTION OF THE INVENTION

Figure 1:
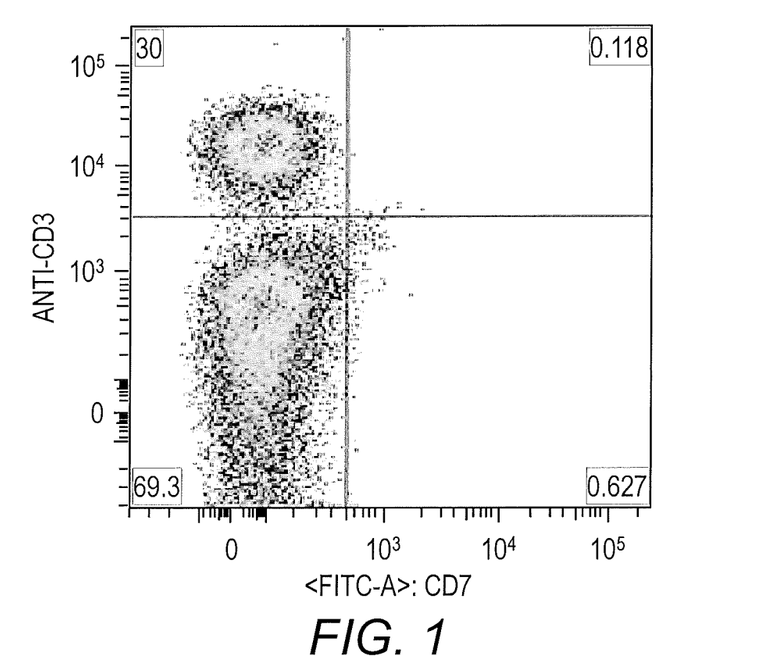
FIG. 1 shows the separation of CD7⁻ cells from peripheral blood mononuclear cell (PBMC) using magnetic cell separation kit from Miltenyi Biotec.
Figure 2A:
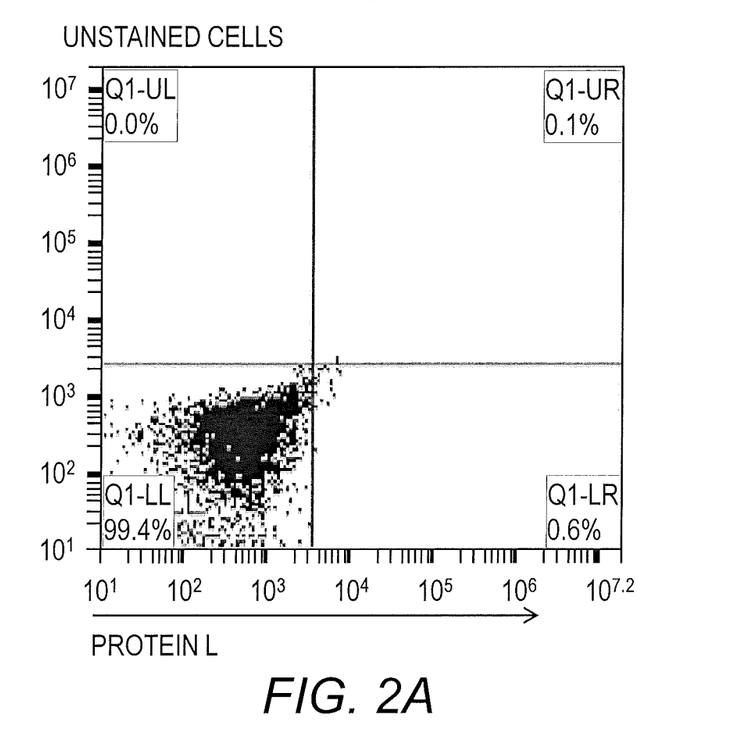
FIG. 2A, FIG. 2B and FIG. 2C show that CD7⁻ cells were transduced with anti-CD7 chimeric antigen receptor (CAR). The transduction efficiency of cells transduced with the anti-CD7 CAR (FIG. 2C) was assessed by protein L staining. Unstained (FIG. 2A) and untransduced cells (FIG. 2B) were used as controls.
Figure 2B:
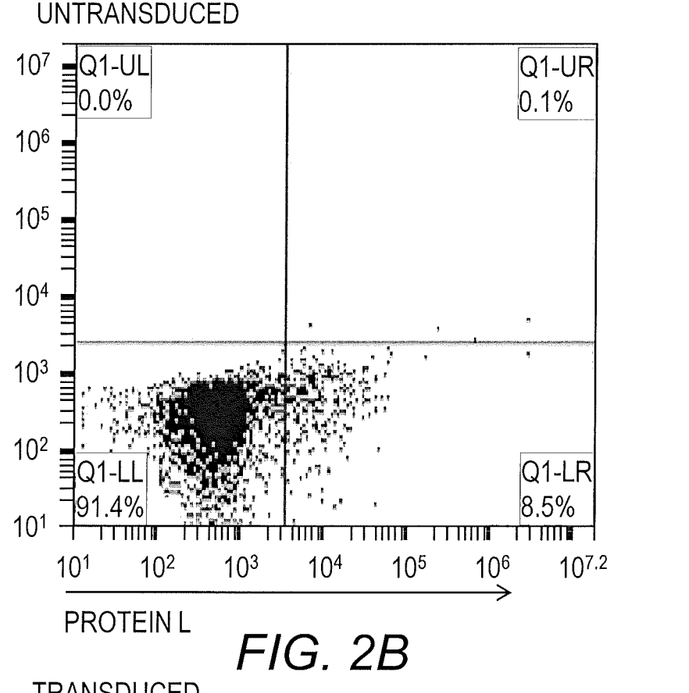
Figure 2C:
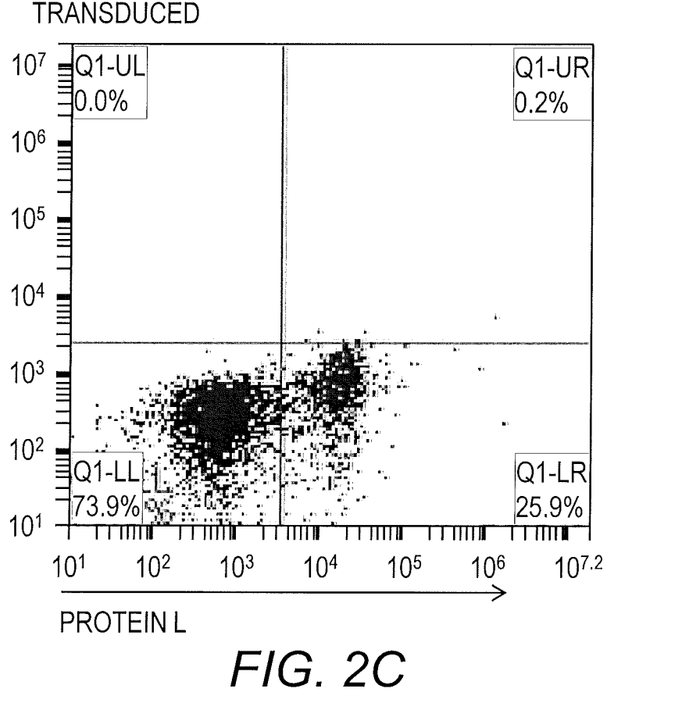
Figure 3:
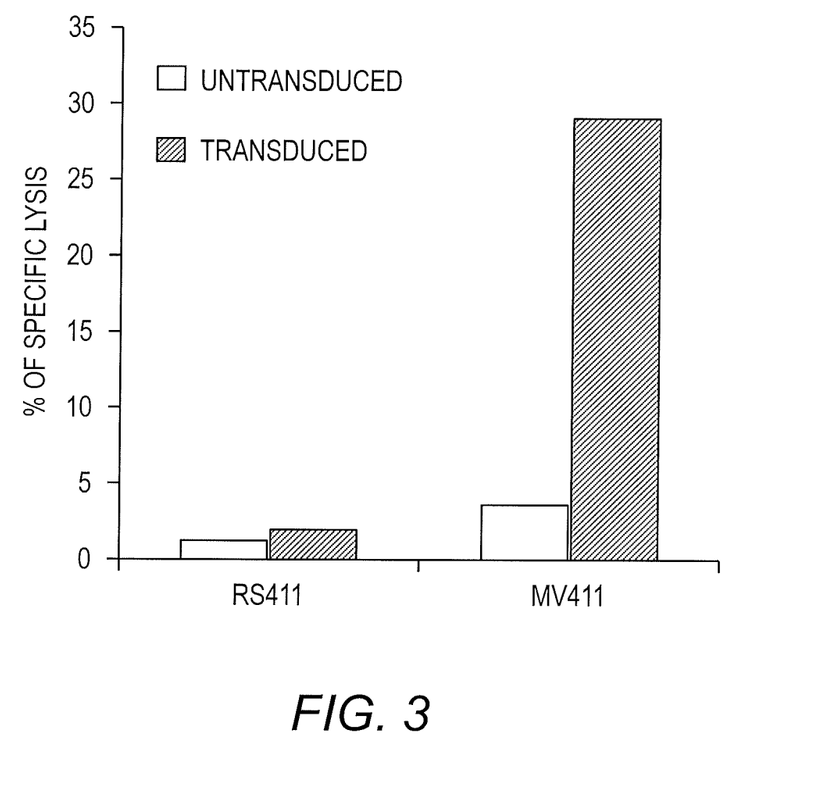
FIG. 3 shows specific killing of CD7⁻ cells transduced with anti-CD7-CAR as assessed against RS411, which do not express CD7, and MV411, which express CD7. Untransduced CD7⁻ cells were used as controls.

CD7⁻ cells were isolated by AUTOMACS (FIG. 1) and transduced with a construct encoding an anti-CD7 CAR (FIG. 2A-FIG. 2C). Upon incubation of the anti-CD7 CAR-transduced cells with the human B cell precursor leukemia cell line RS411, which does not express CD7, and human acute myelocytic leukemia cell line MV411, which does express CD7, it was shown that the anti-CD7 CAR kills cells expressing CD7 (FIG. 3). Accordingly, this invention generally relates to compositions and methods for treating cancer. More specifically, the present invention relates to a nucleic acid construct encoding a CAR, artificial T cell receptor, chimeric T cell receptor, or chimeric immunoreceptor and use of the same to treat cancers including, but not limited to, hematologic malignancies and solid tumors.

A CAR of this invention is composed of an extracellular and intracellular domain. The extracellular domain includes a target-specific binding element otherwise referred to as an antigen recognition domain or antigen binding domain. The intracellular domain, or otherwise the cytoplasmic or endodomain domain, includes a costimulatory signaling domain and a zeta chain portion. The costimulatory signaling domain refers to a portion of the CAR including the intracellular domain of a costimulatory molecule. Costimulatory molecules are cell surface molecules other than antigens receptors or their ligands that are required for an efficient response of lymphocytes to antigen.

Antigen recognition or antigen targeting by CAR molecules most commonly involves the use of an antibody or antibody fragment. However, alternative targeting moieties are also contemplated, including, e.g., ligands such as the K12 protein (U.S. Pat. No. 6,762,030) or Galectin I (Pace, et al. (2000) J. Immunol. 165:2331-2334), peptides, chimeric ligands, and receptor derivatives. In accordance with the present invention, the antigen recognition domain is an antibody or antibody fragment that specifically binds CD7. As used herein, an antibody refers to an immunoglobulin molecule, which specifically binds an antigen. Antibodies can be intact immunoglobulins derived from natural sources or from recombinant sources and can be immunoreactive portions of intact immunoglobulins. Antibodies are typically tetramers of immunoglobulin molecules. An antibody in this invention includes both polyclonal and monoclonal antibodies and humanized antibodies (Harlow, et al. (1999) In: Using Antibodies: A Laboratory Manual, Cold Spring Harbor Laboratory Press, NY; Harlow, et al. (1989) In: Antibodies: a Laboratory Manual, Cold Spring Harbor, New York; Houston, et al. (1988) Proc. Natl. Acad. Sci. USA 85:5879-5883; Bird, et al. (1988) Science 242:423-426).

The term "antibody fragment" refers to a portion of an intact antibody and refers to the antigenic determining variable regions of an intact antibody. Examples of antibody fragments include, but are not limited to, Fab, Fab', F(ab')₂, and Fv fragments, linear antibodies, scFv antibodies, and multispecific antibodies formed from antibody fragments.

Preferably, the antigen recognition domain of the CAR of the invention is an anti-CD7 scFV. In one embodiment, the antibody from which the scFV is derived binds to the extracellular portion of human CD7 protein, e.g., as set forth in GENBANK Accession No. NP_006128. Exemplary anti-CD7 antibodies that specifically bind the extracellular portion of human CD7 include, but are not limited to HuLy-m2 (Thurlow, et al. (1984) *Transplantation* 38:143-147), 3A1 (Ramakrishnan, et al. (1985) *J. Immuol.* 135:3616-3622; Haynes, et al. (1980) *Proc. Natl. Acad. Sci. USA* 77(5):2914-8) and TH-69 (Peipp, et al. (2002) *Cancer Res.* 62:2848-2855). The scFv can be derived from the variable heavy chain (VH) and variable light chain (VL) regions of a CD7-specific monoclonal antibody linked by a flexible linker. The scFv retains the same specificity and a similar affinity as the full antibody from which it was derived (Muniappan, et al. (2000) *Cancer Gene Ther.* 7:128-134). Various methods for preparing an scFv can be used including methods described in U.S. Pat. No. 4,694,778; Bird, et al. (1988) *Science* 242:423-442; Ward, et al. (1989) *Nature* 334:54454; and Skerra, et al. (1988) *Science* 242:1038-1041. In certain embodiments, the scFv is humanized or is a fully human scFv. The nucleic acid and protein sequences of exemplary anti-CD7 scFV molecules are presented in SEQ ID NO:1 and SEQ ID NO:2, respectively.

The CAR is further designed to include a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, a CD3ζ chain, CD28, CD3ε, CD45, CD4, CD5, CD8, CD9, CD16, CD22, CD33, CD37, CD64, CD80, CD86, CD134, CD137, ICOS, CD154, H2-Kb, FcεRIγ or a GITR. See, e.g., Kahlon, et al. (2004) *Cancer Res.* 64:9160-9166; Schambach, et al. (2009) *Methods Mol. Biol.* 506:191-205; Jensen, et al. (1998) *Biol. Blood Marrow Transplant* 4:75-83; Patel, et al. (1999) *Gene Ther.* 6:412; Song, et al. (2012) *Blood* 119:696-706; Carpenito, et al. (2009) *Proc. Natl. Acad. Sci. USA* 106: 3360-5; Hombach, et al. (2012) *Oncoimmunology* 1:458-66) and Geiger, et al. (2001) *Blood* 98:2364-71. Alternatively, the transmembrane domain may be synthetic, in which case it will include predominantly hydrophobic residues such as leucine and valine. Preferably a triplet of phenylalanine, tryptophan and valine will be found at each end of a synthetic transmembrane domain. In certain embodiments, the transmembrane domain of the CAR is all or a portion of the CD28 transmembrane domain (GENBANK Accession No. NP_006130). The nucleic acid and protein sequences of exemplary CD28 transmembrane domains are presented in SEQ ID NO:1 and SEQ ID NO:2, respectively.

The cytoplasmic, endodomain, or intracellular signaling domain of the CAR of the invention is responsible for activation of at least one of the normal effector functions of an immune cell. The term "effector function" refers to a specialized function of a cell. Effector function of a T cell, for example, may be cytolytic activity or helper activity including the secretion of cytokines. Thus, the term "cytoplasmic domain" refers to the portion of a protein which transduces the effector function signal and directs the cell to perform a specialized function. While usually the entire cytoplasmic domain can be employed, in many cases it is not necessary to use the entire chain. To the extent that a truncated portion of a cytoplasmic domain is used, such truncated portion may be used in place of an intact chain as long as it transduces the effector function signal. The term cytoplasmic domain is thus meant to include any truncated portion of a cytoplasmic domain sufficient to transduce the effector function signal. Preferred examples of cytoplasmic domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

Often, signals generated through the TCR alone are insufficient for full activation of the T cell. Accordingly, a secondary or co-stimulatory signal is used. Thus, T cell activation can be said to be mediated by two distinct classes of cytoplasmic signaling sequences: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling domains that act in a stimulatory manner may contain signaling motifs, which are known as immunoreceptor tyrosine-based activation motifs or ITAMs ((Asp/Glu)-Xaa-Xaa-Tyr*-Xaa-Xaa-(Ile/Leu)-Xaa$_{6-8}$-Tyr*-Xaa-Xaa-(Ile/Leu); SEQ ID NO:3) (Reth, et al. (1989) *Nature* 338:383-384). Examples of ITAM-containing primary cytoplasmic signaling domains that are of particular use in the invention include those derived from TCR zeta, CD3λ, FcRγ, FcRβ, CD3γ, CD3δ, CD3ε, CD5, CD22, CD79a, CD79b, and CD66d. Specific examples of the ITAM-containing primary cytoplasmic signaling domains include residues 51 to 164 of CD3ζ (GENBANK Accession No. NP_932170), residues 45 to 86 of FcεRIγ (GENBANK Accession No. NP_004097), residues 201 to 244 of FcεRIβ (GENBANK Accession No. NP_000130), residues 139 to 182 of CD3γ (GENBANK Accession No. NP_000064), residues 128 to 171 of CD3δ (GENBANK Accession No. NP_000723), residues 153 to 207 of CD3ε (GENBANK Accession No. NP_000724), residues 402 to 495 of CD5 (GENBANK Accession No. NP_055022), residues 707 to 847 of CD22 (GENBANK Accession No. NP_001762), residues 166 to 226 of CD79a (GENBANK Accession No. NP_001774), residues 182 to 229 of CD79b (GENBANK Accession No. NP_000611), and residues 177 to 252 of CD66d (GENBANK Accession No. NP_001806), and their variants having the same function as these peptides have. The referenced residues are based on amino acid sequence information from GENBANK and is based on the full length of the precursor (including a signal peptide sequence etc.) of each protein.

The co-stimulatory signaling domain refers to a portion of the CAR including the intracellular domain of a co-stimulatory molecule. A co-stimulatory molecule is a cell surface molecule other than an antigen receptor or their ligands that is required for an efficient response of lymphocytes to an antigen. Examples of such molecules include CD2, CD4, CD5, CD8α, CD8β, CD27, CD28, 4-1BB (CD137), OX40, CD30, CD40, PD-1, ICOS, lymphocyte function-associated antigen-1 (LFA-1), LIGHT, NKG2C, B7-H3, and a ligand that specifically binds with CD83, and the like. Specific examples thereof include residues 236 to 351 of CD2 (GENBANK Accession No. NP_001758), residues 421 to 458 of CD4 (GENBANK Accession No. NP_000607), residues 402 to 495 of CD5 (GENBANK Accession No. NP_055022), residues 207 to 235 of CD8α (GENBANK Accession No. NP_001759), residues 196 to 210 of CD83 (GENBANK Accession No. AAA35664), residues 181 to 220 of CD28 (GENBANK Accession No. NP_006130), residues 214 to 255 of CD137 (4-1BB, GENBANK Accession No. NP_001552), residues 241 to 277 of CD134 (OX40, GENBANK Accession No. NP_003318), and residues 166 to 199 of ICOS (GENBANK Accession No. NP_036224), and their variants having the same function as these peptides have. In some embodiments, the co-stimulatory endodomain of this invention is from CD28, 4-1BB, OX40, ICOS, or a combination thereof.

In a preferred embodiment, the cytoplasmic domain of the CAR is designed to include the CD3ζ signaling domain by itself or combined with any other desired cytoplasmic domain(s) useful in the context of the CAR of the invention. For example, the cytoplasmic domain of the CAR can include a CD3ζ chain portion and a co-stimulatory signaling region. In one embodiment, the cytoplasmic domain is designed to include the signaling domain of CD3ζ and the signaling domain of CD28. In another embodiment, the cytoplasmic domain is designed to include the signaling domain of CD3ζ and the signaling domain of 4-1BB. The nucleic acid sequences of exemplary cytoplasmic domains composed of CD3ζ and 4-1BB are presented in SEQ ID NO:1. The protein sequences of exemplary cytoplasmic domains composed of CD3ζ and 4-1BB are presented in SEQ ID NO:2.

Between the extracellular domain and the transmembrane domain of the CAR, and/or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or the cytoplasmic domain in the polypeptide chain. A spacer domain may be up to 300 amino acids, preferably 2 to 100 amino acids and most preferably 2 to 10 amino acids.

In addition to the antigen binding domain, transmembrane domain, cytoplasmic domain, and spacer domains, the CAR of the invention can also include a signal peptide sequence linked to the N-terminus of the CAR. Signal peptide sequences exist at the N-terminus of many secretory proteins and membrane proteins, and typically have a length of 15 to 30 amino acids. Since many of the protein molecules mentioned above have signal peptide sequences, these signal peptides can be used as a signal peptide for the CAR of this invention.

As will be appreciated by one of skill in the art, in some instances, a few amino acids at the ends of the antigen targeting domain can be deleted, usually not more than 10, more usually not more than 5 residues. Also, it may be desirable to introduce a small number of amino acids at the borders, usually not more than 10, more usually not more than 5 residues. The deletion or insertion of amino acids will usually be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

The sequences of the open reading frames encoding the CAR can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld (2003) J. Immunol. 171(7):3612-9). Also, it may be further advantageous to use endogenous or exogenous noncoding regions to stabilize the mRNA.

In certain embodiments, this invention encompasses a nucleic acid construct encoding sequences of the CAR. For the purposes of this invention, a "nucleic acid" refers to a single or double stranded nucleic acid molecule, which is isolated and provided in the form of RNA, a complementary polynucleotide (cDNA), a genomic polynucleotide and/or a composite polynucleotide (e.g., a combination of the above). As used herein, the term "nucleic acid construct" refers to a nucleic acid molecule, which includes nucleic acids encoding an anti-CD7 CAR. In some embodiments, the nucleic acid construct is a linear naked molecule or a vector, e.g., a plasmid, a bacmid, a phagemid, a cosmid, a phage, a virus or an artificial chromosome.

The expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration into eukaryotic cells. Typical cloning vectors contain transcription and translation terminators, initiation sequences, and promoters useful for regulation of the expression of the desired nucleic acid molecule.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors. Further, the expression vector may be provided to a cell in the form of a viral vector. Viral vector technology is well known in the art and is described, for example, in Sambrook, et al. ((2001) Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers. See, e.g., WO 01/96584; WO 01/29058; and U.S. Pat. No. 6,326,193.

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used. Lentiviral vectors have the added advantage over vectors derived from onco-retroviruses such as murine leukemia viruses in that they can transduce non-proliferating cells, such as hepatocytes. They also have the added advantage of low immunogenicity.

In accordance with the present invention, the nucleic acid construct is transformed or introduced into a cell and is transcribed and translated to produce a product (i.e., a chimeric receptor). Thus, the nucleic acid construct further includes at least one promoter for directing transcription of the CAR. Accordingly, in certain embodiments, nucleic acids encoding the CAR are operably linked to a promoter. A coding nucleic acid is "operably linked" to a regulatory sequence (e.g., promoter) if the regulatory sequence is capable of exerting a regulatory effect on the coding sequence linked thereto. In other words, a promoter is positioned so as to promote transcription of the messenger RNA from the DNA encoding the CAR.

The promoter of the invention can be of genomic origin or synthetically generated. A variety of promoters for use in T cells have been described in the art. For example, the CD4 promoter is disclosed by Marodon, et al. ((2003) *Blood* 101(9):3416-23). The promoter can be constitutive or inducible, where induction is associated with the specific cell type, a specific level of maturation, or drug (e.g., tetracycline or doxorubicin). Alternatively, a number of viral promoters are also suitable. One example of a suitable promoter is the immediate early cytomegalovirus (CMV) promoter sequence. This promoter is a strong constitutive promoter capable of driving high levels of expression of any polynucleotide operatively linked thereto. Another example of a suitable promoter is Elongation Growth Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters, inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to, a metallothionine promoter, a glucocorticoid promoter, a progesterone promoter, and a tetracycline promoter.

Additional promoter elements, e.g., enhancers, can also be included in the construct to regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors, in other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei, et al. (2000) *FEBS Letters* 479:79-82).

In some embodiments of the invention, a nucleic acid construct or cell harboring the nucleic acid construct includes a nucleic acid encoding a protein that is capable of triggering cell death or elimination. Examples of such proteins include suicide proteins such as thymidine kinase (TK) of the HSV virus (herpesvirus) type I (Bonini, et al. (1997) *Science* 276:1719-1724), a Fas-based "artificial suicide gene" (Thomis, et al. (2001) *Blood* 97:1249-1257), *E. coli* cytosine deaminase gene or caspase-9, which are activated by ganciclovir, AP1903, 5-fluorocytosine or a specific chemical inducer of dimerization (CID), respectively.

The nucleic acid encoding the protein for cell death or elimination is advantageously provided in the nucleic acid construct of the invention to allow for the opportunity to ablate the transduced T cells in case of toxicity and to destroy the chimeric construct once a tumor has been reduced or eliminated. The use of suicide genes for eliminating transformed or transduced cells is described in the art. For example, Bonini, et al. ((1997) *Science* 276:1719-1724) teach that donor lymphocytes transduced with the HSV-TK suicide gene provide antitumor activity in patients for up to one year and elimination of the transduced cells is achieved using ganciclovir. Further, Gonzalez, et al. ((2004) *J. Gene Med.* 6:704-711) describe the targeting of neuroblastoma with cytotoxic T lymphocyte clones genetically modified to express a chimeric scFvFc:ζ immunoreceptor specific for an epitope on L1-CAM, wherein the construct further expresses the hygromycin thymidine kinase (HyTK) suicide gene to eliminate the transgenic clones.

It is contemplated that the nucleic acid encoding the protein for cell death or elimination can be expressed from the same promoter as the CAR or from a different promoter. Generally, however, nucleic acid encoding the protein for cell death or elimination and CAR reside on the same construct or vector.

The simultaneous or co-expression of a CAR and a protein for cell death or elimination via a single promoter may be achieved by the use of an internal ribosomal entry site (IRES) or cis-acting hydrolase element. The term "internal ribosome entry site" or "IRES" defines a sequence motif that promotes attachment of ribosomes to that motif on internal mRNA sequences. Consequently, an mRNA containing an IRES sequence motif results in two translational products, one initiating from the 5'-end of the mRNA and the other by an internal translation mechanism mediated by the IRES. A number of IRES have been described and can be used in the nucleic acid construct of this invention. See, e.g., U.S. Pat. No. 8,192,984; WO 2010/119257; and US 2005/0112095.

A "cis-acting hydrolase element" or "CHYSEL" refers to a peptide sequence that causes a ribosome to release the growing polypeptide chain that it is being synthesizes without dissociation from the mRNA. In this respect, the ribosome continues translating and therefore produces a second polypeptide. Peptides such as the foot and mouth disease virus (FMDV) 2A sequence (GSGSRVTELLYRMKRAETYC PRPLLAIHPTEARHKQKIVAPVKQLLNFDLLKLAGDVESNPGP, SEQ ID NO:4), Sponge (*Amphimedon queenslandica*) 2A sequence (LLCFMLLLLLSGDVELNPGP, SEQ ID NO:5; or HHFMFLLLLL AGDIELNPGP, SEQ ID NO:6); acorn worm (*Saccoglossus kowalevskii*) (WFLVLLSFILSGDIEVNPGP, SEQ ID NO:7) 2A sequence; amphioxus (*Branchiostoma floridae*) (KNCAMYMLLLSGDVETNPGP, SEQ ID NO:8; or MVISQLMLKLAGDVEENPGP, SEQ ID NO:9) 2A sequence porcine teschovirus-1 (GSGATNFSLLKQAGDVEENPGP, SEQ ID NO:10) 2A sequence; *Thoseaasigna* virus (GSGEGRGSLLTCGDVEENPGP, SEQ ID NO:11) 2A sequence; and equine rhinitis A virus (GSGQCTNYALLKLAGDVESNPGP, SEQ ID NO:12) 2A sequence are CHYSELs of use in this invention. In some embodiments, the 2A sequence is a naturally occurring or synthetic sequence that includes the 2A consensus sequence D-X-E-X-NPGP (SEQ ID NO:13), in which X is any amino acid residue.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook, et al. ((2001) *Molecular Cloning: A Laboratory Manual*, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). In the case where a non-viral delivery system is used, an exemplary delivery vehicle is a liposome. The use of lipid formulations is contemplated for the introduction of the nucleic acids into a host cell {in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell, in order to confirm the presence of the nucleic acid construct in the host cell, a variety of assays may be performed. Such assays include, for example, "molecular biological" assays well known to those of skill in the art, such as Southern and northern blot analysis, RT-PCR and PCR; and "biochemical" assays, such as detecting the presence or absence of a particular peptide, e.g., by immunological means (ELISAs and western blot analysis).

The constructs of this invention find application in the treatment of subjects having or suspected of having cancer. Accordingly, the invention further relates to a method to treat cancers including, but not limited to, hematologic malignancies and solid tumors, by delivering to a subject in need of treatment an effective amount of the nucleic acid construct of this invention. The step of delivering the nucleic acid construct to the subject generally involves introducing a nucleic acid construct of the invention into an isolated immune cell (e.g., an autologous or third party-derived T cell) and introducing into the subject the transformed immune cell, thereby effecting anti-tumor responses to reduce or eliminate tumors in the subject.

In particular embodiments, an immune cell used in the treatment of cancer is a T cell. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments, any number of T cell lines available in the art, may be used. In other embodiments, T cells can be obtained from a unit of blood collected from a subject using any number of techniques known to the skilled artisan, such as FICOLL separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets, in one embodiment, the cells collected by apheresis may be washed to remove the plasma fraction and to place the cells in an appropriate buffer or media for subsequent processing steps. In one embodiment, the cells are washed with phosphate-buffered saline (PBS). In an alternative embodiment, the wash solution lacks calcium and may lack magnesium or may lack many if not all divalent cations.

In another embodiment, T cells are isolated from peripheral blood lymphocytes by lysing the red blood cells and depleting the monocytes, for example, by centrifugation through a PERCOLL™ gradient or by counter-flow centrifugal elutriation. A specific subpopulation of T cells, such as CD3+, CD28+, CD4+, CD8+, CD45RA+, and CD45RO+T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62L+, GITR+, and FoxP3+. Alternatively, in certain embodiments, T regulatory cells are depleted by anti-C25 conjugated beads or other similar method of selection.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natal izumab, efalizumab, antiviral agents, chemotherapy, radiation, or immunosuppressive agents. In a further embodiment, the cells are isolated for a patient and frozen for later use in conjunction with (e.g., before, simultaneously or following) bone marrow or stem cell transplantation or T cell ablative therapy using chemotherapy agents.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 7,144,575; 7,067,318; 7,172,869; 7,232,566; 7,175,843; 5,883,223; 6,905,874; 6,797,514; 6,867,041; and US 2006/0121005. Generally, the T cells of the invention are expanded by contact with a surface having attached thereto an agent that stimulates a CD3 TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, 4-1BBL (CD137) is a suitable ligand for 4-1BB, and CD80 (B7-1) and CD86 (B7-2) are known ligands of CD28.

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, US 2004/0101519 and US 2006/0034810 for artificial antigen presenting cells (aAPCs) of use in activating and expanding T cells. In one embodiment, agents for providing the primary stimulatory signal and the co-stimulatory signal are immobilized on beads, either on the same bead, i.e., "cis," or to separate beads, i.e., "trans."

The present invention also encompasses a cell (e.g., T cell) transduced with a nucleic acid construct encoding an anti-CD7 CAR. In some embodiments, the nucleic acid construct is a lentiviral vector (LV) harboring nucleic acids encoding an anti-CD7 CAR. For example, the LV encodes a CAR that combines an antigen recognition domain of a specific antibody with an intracellular domain of CD3ζ, CD28, 4-1BB, or any combinations thereof. Therefore, in some instances, the transduced T cell can elicit a CAR-mediated T-cell response.

In particular embodiments, the present invention provides a method for producing an anti-CD7 CAR T cell, wherein the method includes the steps of obtaining a population of CD7-negative T cells and transducing the CD7-negative T cells with a nucleic acid construct encoding an anti-CD7

CAR. For the purposes of the present invention, a population of CD7-negative T cells refers to a population of T cells that are substantially negative of CD7 expression. The phrase "substantially negative of CD7 expression" is intended to mean that less than about 5%, 4%, 3%, 2%, 1%, or even 0% of the cells in the population express the CD7. CD7-negative T cells can be isolated using a single negative depletion step, e.g., as exemplified herein. In accordance with one embodiment, a population of cells (e.g., PBMC) is a labeled with an anti-CD7 antibody and cells labeled with the anti-CD7 antibody are separated from unlabeled cells. Cell sorting can be carried out using any suitable method including single cell sorting (e.g., using an IsoRaft array or DEPArray lab-on-a-chip), fluorescent activated cell sorting (e.g., using flow cytometry), or magnetic cell sorting.

The invention provides the use of a CAR to redirect the specificity of a primary T cell to a tumor antigen, Thus, the present invention also provides a method for stimulating a T cell-mediated immune response to a target cell population or tissue in a mammal by administering to the mammal a T cell that expresses an anti-CD7 CAR, wherein the CAR has a binding moiety that specifically interacts with CD7, a zeta chain portion including for example the intracellular domain of human CD3, and a costimulatory signaling region.

The present invention also includes a type of cellular therapy where T cells are genetically modified to express a CAR and the CAR T cell is infused to a recipient in need thereof. The infused cell is able to kill tumor cells in the recipient. Unlike antibody therapies, CAR T cells are able to replicate in vivo resulting in long-term persistence that can lead to sustained tumor control. In one embodiment, the CAR T cells of the invention can undergo robust in vivo T cell expansion and can persist for an extended amount of time.

Without wishing to be bound by any particular theory, the anti-tumor immunity response elicited by the CAR-modified T cells may be an active or a passive immune response. In addition, the CAR-mediated immune response may be part of an adoptive immunotherapy approach in which CAR-modified T cells induce an immune response specific to the antigen binding moiety in the CAR. For example, cells expressing an anti-CD7 CAR elicit an immune response specific against cells expressing CD7, in particular cancer cells. Cancers that may be treated in accordance with this invention include tumors that are not vascularized, or not yet substantially vascularized, as well as vascularized tumors. The cancers include non-solid tumors (such as hematological tumors, for example, leukemias and lymphomas), which express CD7, as well as solid tumors such as malignant mesothelioma, which expresses CD7 (Hibi, et al. (1992) *Jpn. J. Cancer Res.* 83:680-3). Types of cancers to be treated with the CARs of the invention include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included, Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblasts, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

CAR-modified T cells of the present invention may be administered either alone, or as a pharmaceutical composition in combination with diluents and/or with other components such as IL-2 or other cytokines or cell populations. Briefly, pharmaceutical compositions of the present invention may include CAR-modified T cells as described herein, in combination with one or more pharmaceutically or physiologically acceptable carriers, diluents or excipients. Such compositions may include buffers such as neutral-buffered saline, phosphate-buffered saline and the like; carbohydrates such as glucose, mannose, sucrose or dextrans, mannitol; proteins; polypeptides or amino acids such as glycine; antioxidants; chelating agents such as EDTA or glutathione; and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When a "therapeutic amount" is indicated, the precise amount of the compositions of the present invention to be administered can be determined by a physician with consideration of individual differences in age, weight, tumor size, and condition of the patient (subject). It can generally be stated that a pharmaceutical composition including the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg, et al. (1988) *New Eng. J. Med.* 319:1676). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc, Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to chemotherapy; radiation; immunosuppressive agents, such as cyclosporin, azathioprine, methotrexate, mycophenolate, and FK506; antibodies, or other immunoablative agents. In a further embodiment, the cell compositions of the present invention can be administered to a patient in conjunction with (e.g., before, simultaneously or following) bone marrow transplantation, T cell ablative therapy using either chemotherapy agents such as fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., rituximab. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

The following non-limiting examples are provided to further illustrate the present invention.

EXAMPLE 1

Protocol for CD7⁻ Cell Separation

Peripheral blood mononuclear cells (PBMCs) were isolated by density gradient centrifugation using FICOLL-PAQUE. CD7⁻ cells were isolated from PBMCs. In the first step, the PBMCs were labeled with biotinylated anti-CD7 antibody followed by labeling with anti-biotinylated magnetic beads. Subsequently, the cells were separated by autoMACS (Miltenyi Biotec).

Labeling of cells With Anti-CD7-Biotin. Cell numbers were determined. Cell suspensions were centrifuged at 300×g for 10 minutes. The supernatant was completely aspirated. Nucleated cells were resuspended to $10^7$ cells per 100 μL of buffer. Ten microliters of the biotinylated anti-CD7 antibody was added per $10^7$ cells. The cells were mixed well and subsequently incubated for 15 minutes in the dark in the refrigerator (2-8° C.). Cells were washed by adding staining buffer and centrifuged at 300×g for 10 minutes. The supernatant was completely aspirated and the washing step was repeated. The resulting cells were sequently labeled with anti-biotin magnetic beads.

Procedure for Labeling with Anti-Biotin Magnetic Beads. An appropriate amount of the cell pellet was resuspended in 80 μL of buffer per $10^7$ total cells. To the cells was added 20 μL of Anti-Biotin MicroBeads (Miltenyi Biotec) per $10^7$ total cells. The cells were mixed well and incubated for 15 minutes in the refrigerator (2-8° C.). The cells were washed by adding 2 mL of buffer per $10^7$ cells and subsequently centrifuged at 300×g for 10 minutes. The supernatant was aspirated completely. Cells ($10^8$) were resuspended in 500 μL of buffer and subsequently separated with an AUTOMACS Separator.

Magnetic Separation with the AUTOMACS Separator. The instrument was prepared and primed. Tubes containing the sample and for collecting the labeled and unlabeled cell fractions were placed in the machine. The deplete program of the AUTOMACS Separator was run, the negative fraction was collected, and the purity of the isolated cells was assessed using flow cytometry analysis.

What is claimed is:

1. An isolated nucleic acid construct encoding a chimeric antigen receptor (CAR) comprising an anti-CD7 binding domain, a transmembrane domain, and a cytoplasmic domain, wherein said CAR comprises the amino acid sequence of SEQ ID NO:2.

2. The nucleic acid construct of claim 1, wherein the construct comprises a vector.

3. A mammalian cell comprising the nucleic acid construct of claim 1.

4. The mammalian cell of claim 3, wherein the cell is a T cell, a Natural Killer cell, a cytotoxic T lymphocyte, or a regulatory T cell.

5. A method for producing an anti-CD7 chimeric antigen receptor (CAR) T cell comprising
 (a) obtaining a population of CD7-negative T cells; and
 (b) transducing the CD7-negative T cells with a nucleic acid construct encoding an anti-CD7 CAR comprising the amino acid sequence of SEQ ID NO:2.

6. A method for treating a CD7 expressing hematological cancer comprising delivering to a subject in need of treatment an effective amount of a T cell, a Natural Killer cell, or a cytotoxic T lymphocyte, said cell comprising the nucleic acid construct of claim 1, thereby treating the subject's cancer.

* * * * *